United States Patent [19]

Lazer et al.

[11] Patent Number: 5,741,798
[45] Date of Patent: Apr. 21, 1998

[54] 2-BENZYL-4-SULFONYL-4H-ISOQUINOLIN-1,3-DIONES AND THEIR USE AS ANTIINFLAMMATORY AGENTS

[75] Inventors: Edward S. Lazer, Trumbull; Charles Cywin; Ronald J. Sorcek, both of Bethel, all of Conn.

[73] Assignee: Boehringer Ingelheim Pharmaceuticals, Inc., Ridgefield, Conn.

[21] Appl. No.: 855,554

[22] Filed: May 13, 1997

[51] Int. Cl.⁶ .................... C07D 217/22; A61K 31/47
[52] U.S. Cl. ................................. 514/309; 546/142
[58] Field of Search ........................ 546/141, 142; 514/307, 309

[56] References Cited

U.S. PATENT DOCUMENTS

| | | | |
|---|---|---|---|
| 3,591,584 | 7/1971 | Lombardino et al. | 260/243 |
| 3,853,862 | 12/1974 | Lombardino | 260/243 R |
| 3,892,740 | 7/1975 | Lombardino | 260/243 R |
| 3,925,371 | 12/1975 | Rasmussen | 260/243 R |
| 3,998,954 | 12/1976 | Kadin | 424/250 |
| 4,067,873 | 1/1978 | Troxler et al. | 260/288 |
| 4,073,909 | 2/1978 | Troxler et al. | 424/258 |
| 4,100,347 | 7/1978 | Hammen | 544/49 |
| 4,198,512 | 4/1980 | Kubo et al. | 546/142 |
| 4,230,711 | 10/1980 | Zhiman | 424/258 |
| 4,233,299 | 11/1980 | Trummlitz et al. | 424/246 |
| 4,843,077 | 6/1989 | Hinkle et al. | 514/253 |
| 4,857,301 | 8/1989 | Czarniecki et al. | 424/40 |
| 4,863,948 | 9/1989 | Arrowsmith et al. | 514/416 |
| 5,298,503 | 3/1994 | Peglion et al. | 514/212 |
| 5,340,811 | 8/1994 | Kajihara et al. | 514/253 |
| 5,362,736 | 11/1994 | Ishikawa et al. | 514/291 |

Primary Examiner—Mark L. Berch
Assistant Examiner—Sabiha N. Qazi
Attorney, Agent, or Firm—Robert P. Raymond; Alan R. Stempel; Mary-Ellen Devlin

[57] ABSTRACT

Antiinflammatory compounds of the formula I or IA

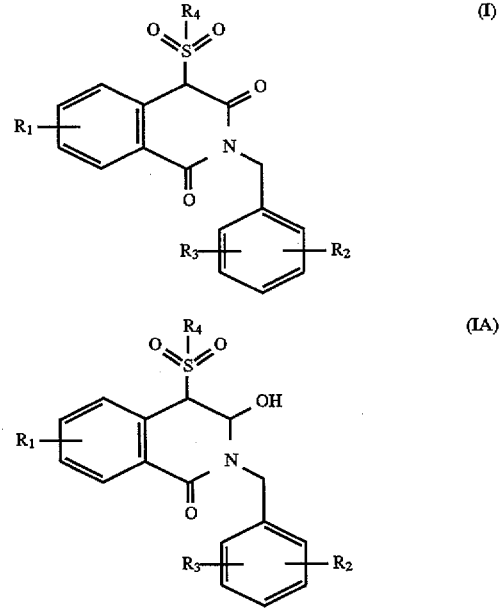

wherein, $R_1$ is hydrogen, halogen, $C_{1-4}$ alkyl, or $C_{1-4}$ alkoxy;

$R_2$ and $R_3$ are the same or different and each is hydrogen, halogen, trifluoromethyl, $C_{1-4}$ alkyl, or $C_{1-4}$ alkoxy; and, $R_4$ is $C_{3-4}$ alkyl, $C_{1-4}$-trifluoroethyl, 2-thienyl, 2-naphthyl, phenyl or phenyl mono- or disubstituted with $C_{1-4}$ alkyl, $C_{1-4}$ alkoxy, halogen, trifluoromethyl, or nitro.

6 Claims, No Drawings

2-BENZYL-4-SULFONYL-4H-ISOQUINOLIN-1,3-DIONES AND THEIR USE AS ANTIINFLAMMATORY AGENTS

RELATED APPLICATIONS

The benefit of provisional application Ser. No. 60/019,131 filed Jun. 3, 1996 is hereby claimed.

FIELD OF THE INVENTION

The invention relates to novel 2-benzyl-4-sulfonyl-4H-isoquinolin-1,3-diones and their use as antiinflammatory agents.

BACKGROUND OF THE INVENTION

Many non-steroidal antiinflammatory drugs (NSAIDs) are currently marketed. They exert their antiinflammatory effect by inhibiting the enzyme cyclooxygenase. These drugs have a beneficial effect in reducing the pain and symptoms of inflammation but they have serious unwanted side effects associated with their use, including gastrointestinal and renal toxicity. Recently a new isoform of cyclooxygenase (COX-2) has been discovered that is thought to be responsible for causing inflammation, and it is thought that much of the toxicity of current NSAIDS is due to their inhibition of COX-1. Most available NSAIDs are not selective in their inhibition of the two COX isoforms or are more potent in inhibiting COX-1.

Recently, there have been discovered agents which more or less selectively inhibit the COX-2 isoform. Exemplary of this new class of compounds is (meloxicam, UHAC62), which is described in U.S. Pat. No. 4,233,299.

SUMMARY OF THE INVENTION

The present invention provides novel compounds having antiinflammatory activity which inhibit both COX-1 and COX-2 approximately equipotently or, in the case of certain preferred compounds, are more selective for COX-2.

DETAILED DESCRIPTION OF THE INVENTION

In its broadest generic aspect, the invention comprises 2-benzyl-4-sulfonyl-4H-isoquinolin-1,3-diones of the formula I or IA

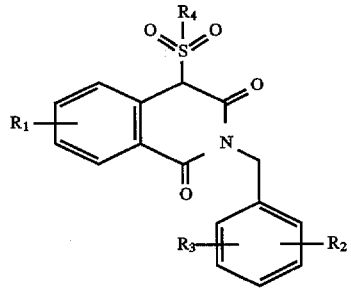
(I)

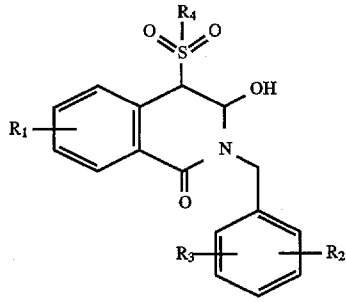
(IA)

wherein, $R_1$ is hydrogen, halogen, $C_{1-4}$ alkyl, or $C_{1-4}$ alkoxy;

$R_2$ and $R_3$ are the same or different and each is hydrogen, halogen, trifluoromethyl, $C_{1-4}$ alkyl, or $C_{1-4}$ alkoxy; and, $R_4$ is $C_{3-4}$ alkyl, 1,1,1-trifluoroethyl, 2-thienyl, 2-naphthyl, phenyl or phenyl mono- or disubstituted with $C_{1-4}$ alkyl, $C_{1-4}$ alkoxy, halogen, trifluoromethyl, or nitro.

It will be appreciated that formulas I and IA represent tautomeric forms of the same compound.

In a first subgeneric aspect, the invention comprises compounds of the above formula I or IA wherein, $R_1$ is hydrogen, fluorine, chlorine, bromine, $C_{1-4}$ alkyl or $C_{1-4}$ alkoxy;

$R_2$ and $R_3$ are the same or different and each is hydrogen, fluorine, chlorine, bromine; trifluoromethyl, $C_{1-4}$ alkyl or $C_{1-4}$ alkoxy; and, $R_4$ is isopropyl, t-butyl, 1,1,1-trifluoroethyl, 2-thienyl, 2-naphthyl, phenyl or phenyl mono- or disubstituted with $C_{1-4}$ alkyl, $C_{1-4}$ alkoxy, fluorine, chlorine, bromine, trifluoromethyl, or nitro.

In a second subgeneric aspect, the invention comprises compounds of the above formula I or IA wherein, $R_1$ is hydrogen, or is in the 6- or 7-position and is fluorine, chlorine, bromine, $C_{1-4}$ alkyl or $C_{1-4}$ alkoxy;

$R_2$ and $R_3$ are the same or different and each is hydrogen, fluorine, chlorine, bromine; trifluoromethyl, $C_{1-4}$ alkyl or $C_{1-4}$ alkoxy; and, $R_4$ is isopropyl, 1,1,1-trifluoroethyl, 2-thienyl, 2-naphthyl, phenyl or phenyl mono- or disubstituted with $C_{1-4}$ alkyl, $C_{1-4}$ alkoxy, fluorine, chlorine, bromine, trifluoromethyl, or nitro.

In a third subgeneric aspect, the invention comprises compounds of the above formula I or IA wherein, $R_1$ is hydrogen, or is in the 6- or 7-position and is fluorine, chlorine, bromine, $C_{1-4}$ alkyl or $C_{1-4}$ alkoxy;

$R_2$ is hydrogen;

$R_3$ is hydrogen, fluorine, chlorine, bromine; trifluoromethyl, $C_{1-4}$ alkyl or $C_{1-4}$ alkoxy; and, $R_4$ is isopropyl, 1,1,1-trifluoroethyl, 2-thienyl, 2-naphthyl, phenyl or phenyl monosubstituted with $C_{1-4}$ alkyl, $C_{1-4}$ alkoxy, fluorine, chlorine, bromine, trifluoromethyl, or nitro.

In accordance with a preferred method, the compounds of the invention may be prepared by reaction of a suitably substituted 2-benzyl-4H-isoquinoline-1,3-dione (II) with an alkyl or aryl sulfonyl halide in the presence of a base, such as, for example, 1,8-diazabicyclo[5.4.0]undec-7ene (DBU), in an inert solvent, such as, for example, methylene chloride, as illustrated by the reaction scheme shown below.

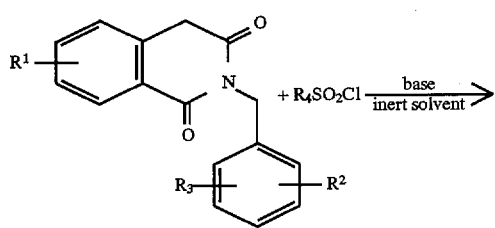

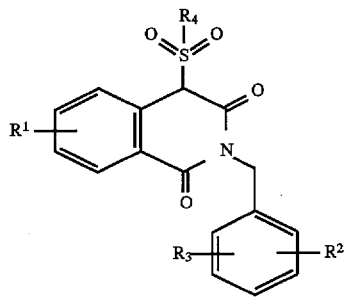

The intermediate II can be prepared by hydrolysis and decarboxylation of the corresponding ester III (the methyl ester is shown, but any ester is suitable) for example by heating with an acid such as 48% HBr.

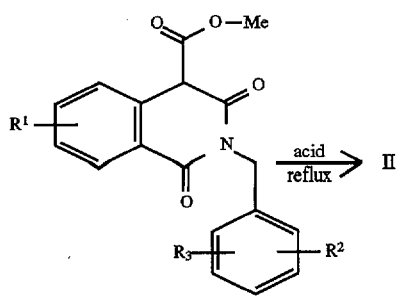

Esters of formula III are known and their preparation is described in the chemical literature (e.g. M. S. Malamas et al., J. Med. Chem. 1994, 37, 2043)

Alternatively II may be prepared by reaction of a suitably substituted homophthalic anhydride (IV) with a suitably substituted benzyl amine (V) in an inert solvent such as toluene.

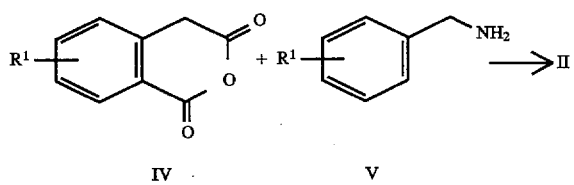

Synthetic Examples

The following examples describe the synthesis of specific compounds in accordance with the invention.

EXAMPLE 1

2-Benzyl-6-chloro-4-(1-methylethyl)sulfonyl-4H-isoquinolin-1,3-dione

Isopropylsulfonyl chloride (140 mg, 0.962mmol) was added to a solution of 250 mg (0.875 mmol) 2-benzyl-6-chloro-4H-isoquinoline-1,3-dione and 270 mg (1.75 mmol) DBU in 2.5 mL methylene chloride under Argon, which was cooled in ice-EtOH to −10° C. After 30 min, the reaction was allowed to warm to room temperature and was stirred overnight. The reaction was diluted with EtOAc, washed three times with 2N HCl dried ($Na_2SO_4$) and concentrated. The residue was triturated with EtOH, petroleum ether was added and the resulting crystals were filtered. Recrystallization from MeOH-petroleum ether gave 186 mg of the title compound, mp 150°–152° C.

EXAMPLE 2

2-(2-Fluorobenzyl)-4-(1-methylethyl)sulfonyl-4H-isoquinoline-1,3-dione

A mixture of 800 mg (4.9 mmol) homophthalic anhydride, 680 mg (5.4 mmol) 2-fluorobenzylamine and 500 mg 4 Å molecular sieves in 1.5 mL toluene was stirred and heated at reflux overnight. A solution of 30% MeOH in $CH_2Cl_2$ was added, the resulting hot mixture filtered and the tiltrate concentrated to give 900 mg 2-(2-fluorobenzyl)-4H-isoquinoline-1,3-dione, mp 140°–144° C. A 500 mg (1.86 mmol) portion of this product was combined with 570 mg (3.71 mmol) DBU in 5 mL $CH_2Cl_2$ under argon, and cooled to −10° C. Isopropylsulfonyl chloride (290 mg, 2.04 mmol) was added, and after stirring 15 min the reaction was allowed to warm to room temperature. After 4 hr the reaction was diluted with EtOAc and worked up as in Example 1 giving 329 mg of the title compound, mp 174°–181° C.

The compounds described in Table 1 were made in an analogous fashion to that described in Examples 1 and 2.

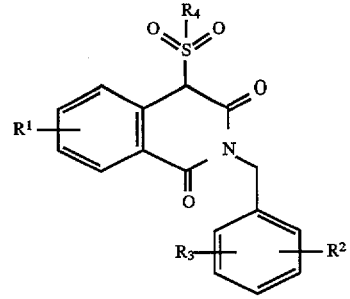

TABLE 1

| Example | $R_1$ | $R_2$ | $R_3$ | $R_4$ | mp (°C.) |
|---|---|---|---|---|---|
| 3 | H | H | H | n-propyl | 147–149 |
| 4 | H | H | H | n-butyl | 127–129 |
| 5 | H | H | H | isopropyl | 210–213 |
| 6 | H | 3-Cl | H | isopropyl | 157–160 |
| 7 | H | 4-Cl | H | isopropyl | 145–149 |
| 8 | H | 4-F | H | isopropyl | 137–141 |
| 9 | H | 3-F | 4-F | isopropyl | 129–133 |
| 10 | 6-Cl | 3-F | 4-F | isopropyl | 145–146 |
| 11 | H | H | H | 1,1,1-trifluoroethyl | 170–200 dec. |
| 12 | H | H | H | phenyl | 181–184 |
| 13 | H | H | H | 4-bromophenyl | 233–236 |
| 14 | H | H | H | 4-methylphenyl | 192–196 |
| 15 | H | H | H | 2-naphthyl | 195–200 |
| 16 | H | H | H | 4-methoxyphenyl | 142–146 |
| 17 | H | H | H | 4-(t-butyl)phenyl | 150–153 |
| 18 | H | H | H | 4-fluorophenyl | 211–214 |
| 19 | H | H | H | 4-chlorophenyl | 237–240 |
| 20 | H | H | H | 4-nitrophenyl | 245–248 |
| 21 | H | H | H | 2-thienyl | 234–237 |

Biological Properties

As mentioned above, the above described compounds of formula I or IA are useful as antiinflammatory agents, by virtue of their ability to inhibit both COX-1 and COX-2 approximately equipotently or, in the case of certain preferred compounds, to inhibit COX-2 to a significantly greater extent than COX-1.

The degree to which compounds inhibit COX-1 and COX-2 can be determined using the in vitro microsomal and cell assay techniques described below.

Microsomal Assay

Human cyclooxygenase 1 and 2 are expressed in a baculovirus expression system using High 5 insect cells. Microsomal fractions prepared from the cells are stored at −80° C. The assays are performed at room temperature in phosphate buffered saline. After incubating the COX-1 or COX-2 microsomes with hematin (2 µM), phenol (0.5 mM) and reduced glutathione (1 mM) for 5 minutes, inhibitor or DMSO vehicle is added and allowed to incubate for 20 minutes. Arachidonic acid (2 µM) is added and after 20 minutes the reaction is stopped by the addition of HCl (0.1 N HCl final concentration). Samples are then diluted in EIA buffer containing 25 µM indomethacin (final concentration) and assayed for $PGE_2$ using Amersham $PGE_2$ EIA extended range protocol (RPN 222).

Cell Assay

Cos-A2 cells stably transfected with human recombinant COX-1 or COX-2 are cultured in 96 well tissue culture plates with Dulbecco's Modified Eagle Medium supplemented with 10% fetal bovine serum, glutamine (2 mM), penicillin (50 U/mL), streptomycin (50 mg/mL) and geneticin (400 µg/mL). Media is removed from confluent monolayers and the cells are washed twice with Hank's buffered saline solution. Fresh HBSS is added, with or without inhibitor, and the cells are incubated for 30 minutes at 37° C. Arachidonic acid (30 µM) is then added and the cells are incubated for an additional one hour at 37° C. Individual experiments represent a mean of triplicate wells for control and inhibitor doses. Supernatents are removed and stored at −80° C. until assayed for $PGE_2$ by EIA (Amersham).

The inhibitory activities against COX-1 and COX-2 of the compounds described in the above Synthetic Examples were determined using the two in vitro assays described above. The results of these tests are given in Tables 2 and 3.

TABLE 2

% Inhibition of COX Enzymes in Microsomal Assays

| Cmpd. of Example | COX-2 | | | COX-1 | | |
|---|---|---|---|---|---|---|
| | concentration of test compound (µgrams/mL) | | | | | |
| | 10 | 1 | 0.1 | 10 | 1 | 0.1 |
| 1 | 97 | 87 | 34 | 57 | 34 | 10 |
| 2 | 49 | 37 | 10 | 18 | 14 | −1 |
| 3 | 27 | 15 | −6 | 33 | 22 | −9 |
| 4 | 20 | 30 | 0 | 15 | 15 | 4 |
| 5 | 58 | 56 | 27 | 23 | 11 | −6 |
| 6 | 27 | 27 | 10 | 30 | 19 | −10 |
| 7 | 67 | 62 | 3 | 36 | 4 | −3 |
| 8 | 86 | 68 | −1 | 47 | 28 | 11 |
| 9 | 80 | 75 | 8 | 57 | 17 | 10 |
| 10 | 100 | 100 | −3 | 96 | 40 | 13 |
| 11 | 52 | 32 | 23 | 50 | 21 | 4 |
| 12 | 72 | 58 | 22 | 74 | 59 | 17 |
| 13 | 100 | 92 | 28 | 100 | 74 | 44 |
| 14 | 100 | 63 | −13 | 100 | 93 | 59 |
| 15 | 34 | 14 | −29 | 57 | 24 | 23 |

TABLE 2-continued

% Inhibition of COX Enzymes in Microsomal Assays

| Cmpd. of Example | COX-2 | | | COX-1 | | |
|---|---|---|---|---|---|---|
| | concentration of test compound (µgrams/mL) | | | | | |
| | 10 | 1 | 0.1 | 10 | 1 | 0.1 |
| 16 | 97 | 74 | 21 | 93 | 81 | 33 |
| 17 | 39 | 12 | 20 | 45 | 20 | 17 |
| 18 | 81 | 66 | 33 | 92 | 76 | 48 |
| 19 | 93 | 89 | 59 | 89 | 71 | 52 |
| 20 | 46 | 37 | 20 | 62 | 41 | 21 |
| 21 | 48 | 46 | 12 | 67 | 14 | 17 |

TABLE 3

Inhibition of COX Enzymes in COS Cell Assays

| Cmpd. of Example | COX-2 | | | COX-1 | | |
|---|---|---|---|---|---|---|
| | % inhibition at 10, 1 and 0.1 µM | | $IC_{50}$ (µM) | % inhibition at 10, 1 and 0.1 µM | | $IC_{50}$ (µM) |
| 5 | 51 | 37 | 17 | — | 74 | 43 | 13 | — |
| 7 | 74 | 52 | 26 | — | 72 | 46 | 6 | — |
| 2 | 46 | 45 | NT | — | 39 | 33 | NT | — |
| 8 | — | — | — | 0.09 | — | — | — | 0.25 |
| 9 | — | — | — | 0.2 | — | — | — | 0.57 |
| 1 | — | — | — | 0.06 | — | — | — | 1.4 |
| 10 | — | — | — | 0.1 | 88 | 55 | 20 | — |
| 11 | 30 | 0 | NT | 64 | 64 | 0 | NT | — |
| 12 | 65 | 48 | 39 | — | 85 | 61 | 22 | — |
| 21 | 89 | 80 | 65 | — | 94 | 67 | 35 | — |

NT = not tested

The antiinflammatory activities of two compounds in accordance with the invention (those of Examples 1 and 10) were determined in vivo and compared to those of the known antiinflammatory agents indomethacin and meloxicam, using the Carrageenan-Induced Paw Edema in Rats protocol described by C. A Winter et al. *J. Pharmacol. Exp. Ther.* 1963, 141, 369. Test compounds were administered orally. The results of this testing are reported in Table 4.

TABLE 4

Effect of Compounds in Carrageenen Paw Edema in Rats

| Compound | Dose (mg/kg) | % Inhibition |
|---|---|---|
| Ex. 1 | 30 | 42.5* |
| Ex. 10 | 30 | 38.6* |
| Indomethacin | 10 | 58* |
| Meloxicam | 30 | 56* |

*$p < 0.05$

The compounds of the present invention are useful for the treatment of inflammation. Such use constitutes another aspect of the invention.

The compounds of the invention (compounds of formula I or IA) may be administered by the oral, parenteral or rectal routes, as active ingredients in customary dosage unit compositions, that is, compositions in dosage unit form comprising an inert pharmaceutical carrier and one effective dosage unit of the active ingredient, such as tablets, coated pills, capsules, wafers, powders, solutions, suspensions, emulsions, syrups, suppositories and the like. One effective oral dosage unit of the compounds according to the present invention is from 0.03 to 7.5 mg/kg body weight, preferably 0.08 to 1.5 mg/kg body weight. The daily dose rate is from 0.08 to 15.0 mg/kg, preferably 0.16 to 3.0 mg/kg.

The compounds of the invention may be administered either alone or in combination with other antiinflammatory agents.

Another aspect of the invention constitutes the preparation of pharmaceutical dosage forms suitable for administration of compounds in accordance with the invention. The following Pharmaceutical Examples describe the preparation of representative pharmaceutical dosage forms. These examples are not intended to limit the scope of the invention. Those skilled in the art will understand how other formulations can be made.

Pharmaceutical Examples

EXAMPLE A

Tablets

The tablet compostion is compounded from the following ingredients:

| Ingredient | Parts |
| --- | --- |
| Compound of Ex. 1 | 10.0 |
| Corn Starch | 112.0 |
| Polyvinylpyrrolidone | 175.0 |
| Magnesium Stearate | 3.0 |
| Total | 300.0 |

Preparation:

The active ingredient and the corn starch are intimately admixed with each other, the mixture is moistened with an aqueous 14% solution of the polyvinylpyrrolidone, and the moist mass is granulated through a 1.5 mm-mesh screen. The moist granulate is dried at 45° C. and again passed through the screen, admixed with the magnesium stearate, and the mixture is compressed into 300 mg tablets. Each tablet is an oral dosage unit composition containing 10 mg of the active ingredient.

EXAMPLE B

Coated Pills

The pill core compostion is compounded from the following ingredients:

| Ingredient | Parts |
| --- | --- |
| Compound of Example 1 | 10.0 |
| Corn starch | 260.0 |
| Gelatin | 8.0 |
| Talcum | 18.0 |
| Magnesium stearate | 4.0 |
| Total | 300.0 |

Preparation:

The active ingredient and the corn starch are intimately admixed with each other, the mixture is moistened with an aqueous 10% solution of the gelatin and the moist mass is granulated through a 1.5 mm-mesh screen. The moist granulate is dried at 45° C., again passed through the screen, admixed with the talcum and the magnesium stearate, and the composition is compressed into 300 mg pill cores which are subsequently coated with a thin shell consisting essentially of a mixture of talcum and sugar, and finally polished with beeswax. Each coated pill is an oral dosage unit composition containing 10 mg of the active ingredient.

EXAMPLE C

Gelatin Capsules

The capsule filler composition is compounded from the following ingredients:

| Ingredient | Parts |
| --- | --- |
| Compound of Example 1 | 5.0 |
| Corn Starch | 385.0 |
| Colloidal silicic acid | 6.0 |
| Magnesium stearate | 4.0 |
| Total | 400.0 |

Preparation:

The ingredients are intimately admixed with each other by milling, and 400 mg portions of the mixture are filled into No. 1 gelatin capsules. Each capsule is an oral dosage unit composition containing 5 mgm of the active ingredient.

EXAMPLE D

Suppositories

The suppository composition is compounded from the following ingredients:

| Ingredient | Parts |
| --- | --- |
| Compound of Example 1 | 25.0 |
| Suppository base (e.g. cocoa butter) | 1725.0 |
| Total | 1750.0 |

Preparation:

The finely pulverized active ingredient is homogeneously blended with the aid of an immersion homogenizer into the suppository base which had been melted and cooled to 40° C. The composition is cooled to 38° C., and 1.75 gm portions thereof are poured into cooled suppository molds and allowed to harden therein. Each suppository is a rectal dosage unit composition containing 25 mg of the active ingredient.

We claim:
1. A compound of the formula I or IA

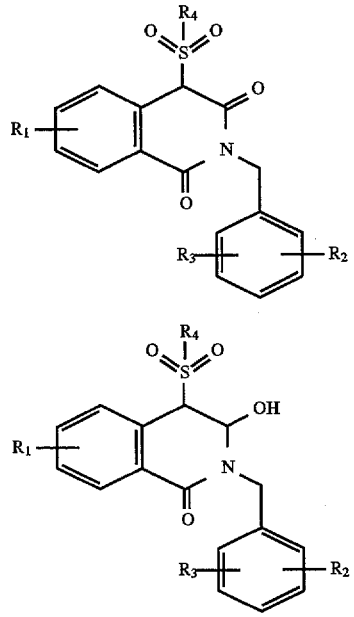

wherein, $R_1$ is hydrogen, halogen, $C_{1-4}$ alkyl, or $C_{1-4}$ alkoxy;

$R_2$ and $R_3$ are the same or different and each is hydrogen, halogen, trifluoromethyl, $C_{1-4}$ alkyl, or $C_{1-4}$ alkoxy; and, $R_4$ is $C_{3-4}$ alkyl, 1,1,1-trifluoroethyl, 2-thienyl, 2-naphthyl, phenyl or phenyl mono- or disubstituted with $C_{1-4}$ alkyl, $C_{1-4}$ alkoxy, halogen, trifluoromethyl, or nitro.

2. A compound of formula I or IA, in accordance with claim 1, wherein:

$R_1$ is hydrogen, or is in the 6- or 7-position and is fluorine, chlorine, bromine, $C_{1-4}$ alkyl or $C_{1-4}$ alkoxy;

$R_2$ and $R_3$ are the same or different and each is hydrogen, fluorine, chlorine, bromine; trifluoromethyl, $C_{1-4}$ alkyl or $C_{1-4}$ alkoxy; and, $R_4$ is isopropyl, 1,1,1-trifluoroethyl, 2-thienyl, 2-naphthyl, phenyl or phenyl mono- or disubstituted with $C_{1-4}$ alkyl, $C_{1-4}$ alkoxy, fluorine, chlorine, bromine, trifluoromethyl, or nitro.

3. A compound of formula I or IA, in accordance with claim 2, wherein:

$R_1$ is hydrogen, or is in the 6- or 7-position and is fluorine, chlorine, bromine, $C_{1-4}$ alkyl or $C_{1-4}$ alkoxy;

$R_2$ is hydrogen;

$R_3$ is hydrogen, fluorine, chlorine, bromine; trifluoromethyl, $C_{1-4}$ alkyl or $C_{1-4}$ alkoxy; and, $R_4$ is isopropyl, 1,1,1-trifluoroethyl, 2-thienyl, 2-naphthyl, phenyl or phenyl monosubstituted with $C_{1-4}$ alkyl, $C_{1-4}$ alkoxy, fluorine, chlorine, bromine, trifluoromethyl, or nitro.

4. A compound selected from the group consisting of:
2-Benzyl-6-chloro-4-(1-methylethyl)sulfonyl-4H-isoquinolin-1,3-dione; and,
2-(2-Fluorobenzyl)-4-(1-methylethyl)sulfonyl-4H-isoquinoline-1,3-dione.

5. A method for treating inflammation which comprises administering to a host in need of such treatment an antiinflammatory amount of a compound in accordance with claim 1, 2, 3 or 4.

6. A pharmaceutical composition comprising a compound in accordance with claim 1, 2, 3 or 4 and a pharmaceutically acceptable carrier.

* * * * *